(12) United States Patent
Lin et al.

(10) Patent No.: US 10,525,073 B2
(45) Date of Patent: Jan. 7, 2020

(54) METHOD FOR IMPROVING KIDNEY AND/OR HEART FUNCTION IN PATIENTS WITH KIDNEY DISEASE

(71) Applicants: Cheng-Jui Lin, Taipei (TW); Chih-Jen Wu, Taipei (TW); Chia-Yuan Liu, Taipei (TW); Horng-Yuan Wang, Taipei (TW)

(72) Inventors: Cheng-Jui Lin, Taipei (TW); Chih-Jen Wu, Taipei (TW); Chia-Yuan Liu, Taipei (TW); Horng-Yuan Wang, Taipei (TW)

(73) Assignee: MacKay Memorial Hospital, Taipei (TW)

( * ) Notice: Subject to any disclaimer, the term of this patent is extended or adjusted under 35 U.S.C. 154(b) by 0 days.

(21) Appl. No.: 15/569,148

(22) PCT Filed: Apr. 26, 2016

(86) PCT No.: PCT/CN2016/080228
§ 371 (c)(1),
(2) Date: Oct. 25, 2017

(87) PCT Pub. No.: WO2016/173487
PCT Pub. Date: Nov. 3, 2016

(65) Prior Publication Data
US 2018/0140624 A1   May 24, 2018

Related U.S. Application Data

(60) Provisional application No. 62/152,965, filed on Apr. 26, 2015.

(51) Int. Cl.
*A61K 31/7072* (2006.01)
*A61P 9/00* (2006.01)
*A61P 13/12* (2006.01)

(52) U.S. Cl.
CPC ............ *A61K 31/7072* (2013.01); *A61P 9/00* (2018.01); *A61P 13/12* (2018.01)

(58) Field of Classification Search
CPC .................................................. A61K 31/7072
See application file for complete search history.

(56) References Cited

U.S. PATENT DOCUMENTS

2008/0286230 A1* 11/2008 Sommadossi ....... C07F 9/65586
424/85.2

OTHER PUBLICATIONS

Gane et al., Gastroenterology, 2014, 146, p. 138-146, Available online Sep. 22, 2013. (Year: 2013).*
Lekawanvijit et al., PLoS ONE, 2012, 7(7): e41281, 10 pages. (Year: 2012).*

* cited by examiner

*Primary Examiner* — Jonathan S Lau

(57) ABSTRACT

Disclosed herein is novel use of telbivudine for improving kidney and/or heart function of a subject suffering from a kidney disease, such as acute kidney injury (AKI) or chronic kidney disease (CKD).

6 Claims, 11 Drawing Sheets

(A) Sham group  (B) 5/6 Nephrectomy group  (C) Telbivudine-treated group (D)

METHOD FOR IMPROVING KIDNEY AND/OR HEART FUNCTION IN PATIENTS WITH KIDNEY DISEASE

CROSS-REFERENCE TO RELATED APPLICATIONS

This application is a national stage of PCT international Application No. PCT/CN2016/080228, filed on Apr. 26, 2016 and published in English on Nov. 3, 2016 with the Publication No. WO2016/173487 A1, and claims priority to U.S. Provisional Patent Application No. 62/152,965, filed Apr. 26, 2015, which is incorporated herein by reference in its entirety.

BACKGROUND OF THE INVENTION

1. Field of the Invention

The present disclosure relates to methods for improving kidney and/or heart function of a subject with kidney disease (KD).

2. Description of Related Art

Acute kidney injury (AKI) or acute renal failure is a syndrome characterized by the rapid loss of the kidney's excretory function and is typically diagnosed by the accumulation of end products of nitrogen metabolism (urea and creatinine) or decreased urine output, or both. The primary causes of AKI are diabetes and high blood pressure, which are responsible for up to two-thirds of the cases. In recent years, the prevalence of AKI has increased due to a rising incidence of diabetes mellitus, hypertension (high blood pressure) and obesity, and also due to an aging population. AKI is also common in hospital patients and very common in critically ill patients. No specific therapies have emerged that can attenuate AKI or expedite its recovery; thus, most treatment is purely supportive. Evidence also suggests that patients who have had AKI are at increased risk of subsequent chronic kidney disease (CKD), which is co-morbid with cardiovascular disease, therefore, CKD patients have an increased risk of death from cardiovascular events, for CKD is thought to accelerate the development of heart disease.

Accordingly, there is an unmet need of an agent that may improve the kidney and/or heart function of a subject suffering from a kidney disease, particularly CKD.

SUMMARY

The present disclosure is based, at least in part, the unexpected discovery that telbivudine is capable of reducing the levels of blood urine nitrogen (BUN), serum creatinine (CR), total and free urine toxin (i.e., P-cresyl sulfate and indoxy sulfate), the expression of inflammatory genes (e.g., TIMP-1, COL-1-A1, and/or TGF-β1) and the extent of kidney and/or heart fibrosis; in addition to increasing the contractile function of the heart. Accordingly, telbivudine and/or a composition comprising the same may be used for the manufacture of a medicament for the treatment of kidney disease, including acute kidney injury (AKI) and chronic kidney disease (CKD).

Accordingly, it is the first aspect of the present disclosure to provide a method of improving kidney and/or heart function of a subject suffering from a kidney disease, such as AKI or CKD. The method comprises administering an effective amount of telbivudine, a salt, a solvate, and/or an ester thereof to the subject, for a sufficient period of time, so as to improve kidney and/or heart function of the subject, and thereby alleviate or ameliorate the symptoms associated with the kidney disease.

Accordingly, a further aspect of the present disclosure is directed to the use of telbivudine for the manufacture of a composition or a medicament for improving kidney and/or heart function of a subject. Typically, telbivudine, a salt, a solvate, and/or an ester thereof is present at a level of about 0.1% to 99% by weight, based on the total weight of the composition or medicament. In some embodiments, the telbivudine, a salt, a solvate, and/or an ester thereof is present at a level of at least 1% by weight, based on the total weight of the composition. In certain embodiments, the telbivudine, a salt, a solvate, and/or an ester thereof is present at a level of at least 5% by weight, based on the total weight of the I composition. In still other embodiments, the telbivudine, a salt, a solvate, and/or an ester thereof is present at a level of at least 10% by weight, based on the total weight of the composition. In still yet other embodiments, the telbivudine, a salt, a solvate, and/or an ester thereof is present at a level of at least 25% by weight, based on the total weight of the composition.

The composition or medicament comprising telbivudine, a salt, a solvate and/or an ester thereof may be administered systemically. Systemically administration can be performed by intraperitoneal administration, intravenous administration, intramuscular administration, intra-arterial administration, subcutaneous administration and oral administration.

The present disclosure also provides kits for improving kidney and/or heart function of a subject suffering from a kidney disease, such as AKI or CKD. The kit includes in its container, (a) an effective amount of telbivudine, a salt, a solvate and/or an ester thereof; (b) one or more pharmaceutical acceptable carriers and/or excipients; and (c) instructions for using the kit to improve kidney and/or heart function of its recipients. The instructions may be in a form of pamphlet, tape, CD, VCD or DVD. According to certain embodiments, the telbivudine, a salt, a solvate and/or an ester thereof is in the form suitable for oral ingestion, subcutaneous infusion, intravenous administration, or inhalation.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF PREFERRED EMBODIMENTS

The detailed description provided below in connection with the appended drawings is intended as a description of the present disclosure and is not intended to represent the only forms in which the present disclosure may be constructed or utilized.

In the context of this disclosure, a number of terms shall be used.

The term "telbivudine" and "Sebivo" are used interchangeably throughout this text, in which Sebivo is the trade name of the chemical—telbivudine, both owned by Novartis (Switzerland).

The terms "treatment" and "treating" are used herein to include preventative (e.g., prophylactic), curative, or palliative treatment that results in a desired pharmaceutical and/or physiological effect. Preferably, the effect is therapeutic in terms of partially or completely curing or preventing the apoptosis of kidney cells. Also, the term "treating" as used herein refers to application or administration of the compound or the composition of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. As used herein, the symptom, disease, disorder or condition may be acute kidney injury (AKI), chronic kidney disease (CKD) and/or complication associated therewith, such as anemia and cardiovascular disease (e.g., pericarditis, or heart failure). Treatment is generally "effective" if one or more symptoms or clinical markers are reduced as that term is defined herein.

The terms "compositions," "agent" and "medicament" are used interchangeably herein to refer to a compound or a composition of which, when administered to a subject such as a human or an animal induces a desired pharmacological and/or physiological effect by local and/or systemic action.

The terms "administered," "administering" and "administration" are used interchangeably herein to refer means either directly administering a compound or a composition of the present invention, or administering a prodrug, derivative or analog which will form an equivalent amount of the active compound (e.g., telbivudine) within the body.

The term "subject" and "patient" are used interchangeably in the present disclosure, and refer to an animal including the human species that is treatable with the compositions and/or methods of the present invention. The term "subject" or "patient" intended to refer to both the male and female gender unless one gender is specifically indicated. Accordingly, the term "subject" or "patient" includes, but is not limited to, human, non-human primate such as any mammal, dog, cat, horse, sheep, pig, cow and etc., preferably a human, which may benefit from treatment by the compound of this disclosure.

The term "an effective amount" as used herein refers to an amount effective, at dosages, and for periods of time necessary, to achieve the desired therapeutically result with respect to the treatment of a kidney disease. The effective amount of the active compound (i.e., telbivudine), its salt, ester or solvate may be ranged from about 0.01 mg/Kg/day to about 1,000 mg/Kg/day; preferably from about 0.1 mg/Kg/day to about 500 mg/Kg/day; more preferably from about 1 mg/Kg/day to about 100 mg/Kg/day. The effective amount may vary depends on the route of administration, and/or other the combinational use of other medicaments.

The term "salt" refers herein as a salt which is formed by the interaction of a base including organic or inorganic types of bases, including bases formed from a metal of the IA or IIA group, ammonium and/or N(alkyl)$_4^+$ with an acid (such as telbivudine in this disclosure). The term "ester" herein refers to an ester of telbivudine, in which the ester bond may be formed between the hydroxy group of telbivudine and an organic acid, such as R—COOH, wherein R is a straight or branched $C_{1-6}$ alkyl. The term "solvate" herein refers to a complex formed by the interaction of a compound (such as telbivudine in this disclosure) with surrounding solvent molecules, such as water, ethanol and etc.

Throughout the specification, unless otherwise indicated to the contrary, improving the kidney and/or heart function means a compound (i.e., telbivudine, a slat, a solvate or an ester thereof) or a composition comprising the same is administered to or a method is used for a subject for a period effective to improve the kidney and/or heart function as determined by comparing with the kidney and/or heart function in a subject not being administered the compound or the composition comprising the same. Accordingly, improving kidney function is meant to improve any of the followings, which include but are not limited to, urine production, removal of excess body fluid, removal of waste products from the blood, maintenance of normal blood chemistry, hormone production or a combination thereof. Improving heart function is meant to improve the contractile function of the heart, which refers to the ability of the heart to contract, by which the muscle increases in tension.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure is based, at least in part, unexpected discovery that the known antiviral drug, telbivudine (trade name Sebivo in Europe or Tyzeka in the United States), used in the treatment of hepatitis B infection, may significantly improve the renal and/or heart function of a subject suffering from AKI or CKD, as demonstrated by improvement in a series of measurable parameters of kidney and/or heart function, including a decrease in blood urine nitrogen (BUN), serum creatinine (CR), the levels of total and free urine toxin (i.e., P-cresyl sulfate and indoxy sulfate), and the extent of kidney fibrosis; as well as an increase in the contractile function of the heart. The results indicate that telbivudine and a composition comprising the same is useful as a therapeutic medicament for the treatment and/or prophylaxis of kidney disease, such as CKD.

Accordingly, one aspect of this disclosure is to provide a method of improving kidney and/or heart function of a subject suffering from kidney disease, such as AKI or CKD. The method comprises administering to the subject, preferably a human being, an effective amount of telbivudine, a salt, a solvate and/or an ester thereof, for a sufficient period of time, so as to improve the kidney and/or heart function of the subject and thereby alleviate or ameoliorate the symptoms associated with the kidney disease.

According to embodiments of the present disclosure, telbivudine, a salt, a solvate, and/or an ester thereof is administered to the subject in an amount between 0.01 mg/Kg/day to about 1,000 mg/Kg/day; preferably from about 0.1 mg/Kg/day to about 500 mg/Kg/day; more preferably from about 1 mg/Kg/day to about 100 mg/Kg/day. The amount required to achieve desirable effects (e.g., an improvement in the kidney and/or heart function) in a subject depends on a number of factors, such as the specific application, the mode of administration, and the weight and condition of he subject in need of the treatment (e.g., sex, age, the disease state or severity of the condition to be alleviated and etc.). An effective amount can readily be determined by routine experimentation using a variety of techniques well-known in the art or by the experience of the attending physician. Telbivudine, a salt, a solvate, and/or an ester thereof is administered to the subject, preferably human, by any route that may effectively transports the telbivudine, a salt, a solvate, and/or an ester thereof to the appropriate or desired site of action. Telbivudine, a salt, a solvate, and/or an ester thereof may be administered systemically or directly to the site of injury (i.e., kidney injury or heart injury). Systemically administration can be performed by intraperitoneal administration, intravenous administration, intramuscular administration, intra-arterial administration, subcutaneous administration and oral administration.

Accordingly, a further aspect of the present disclosure is directed to the use of telbivudine, a salt, a solvate, and/or an ester thereof for manufacturing a composition or a medicament for treating kidney disease, such as AKI and CKD. The composition comprises an effective amount of telbivudine, a salt, a solvate and/or an ester thereof; and a pharmaceuticaly acceptable excipient.

In the manufacture of a composition or a medicament of the present disclosure, telbivudine, a salt, a solvate and/or an ester thereof is mixed with a pharmaceuticaly acceptable excipient or carrier, and is prepared in accordance with acceptable pharmaceutical procedures, such as described in Remington's Pharmaceutical Sciences, $17^{th}$ edition, ed. Alfonoso R. Gennaro, Mack Publishing Company, Easton, Pa. (1985). The excipient or carrier must be acceptable in the sense of being compatible with any other ingredients in the composition or the medicament and must not be deleterious to the subject. The excipient or carrier may be a solid, or a liquid, or both, and is preferably formulated with telbivudine, a salt, a solvate and/or an ester thereof, as a multi-dose formulation, for example, a tablet.

In general, the active ingredient, that is, telbivudine, a salt, a solvate and/or an ester thereof, is present at a level of about 0.1% to 99% by weight, based on the total weight of the composition. In some embodiments, the telbivudine, a salt, a solvate and/or an ester thereof is present at a level of at least 1% by weight, based on the total weight of the composition. In certain embodiments, the telbivudine, a salt, a solvate and/or an ester thereof is present at a level of at least 5% by weight, based on the total weight of the composition. In still other embodiments, the telbivudine, a salt, a solvate and/or an ester thereof is present at a level of at least 10% by weight, based on the total weight of the composition. In still yet other embodiments, the telbivudine, a salt, a solvate and/or an ester thereof is present at a level of at least 25% by weight, based on the total weight of the composition.

The composition of the present disclosure may be administered by any suitable route, for example, orally in capsules, suspensions or tablets or by parenteral administration. Parenteral administration can include, for example, systemic administration such as intramuscular, intravenous, subcutaneous, or intraperitoneal injection. The composition can also be administered transdermally either topically or by inhalation (e.g., intrabronichial, intranasal, oral inhalation or intranasal drops), or rectally, alone or in combination with conventional pharmaceutically acceptable excipients. In preferred embodiments, the composition of the present disclosure are administered orally (e.g., dietary) to the subject.

For oral administration, the composition of the present disclosure may be formulated into tablets containing various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Solid composition may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the telbivudine, a salt, a solvate and/or an ester thereof may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For transmucosal administration, the medicament or said pharmaceutical compositions of the present disclosure may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

It will be appreciated that the dosage of the pharmaceutical composition of the present disclosure will vary from patient to patient not only for the particular route of administration, and the ability of the composition to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the composition are outweighed by the therapeutically beneficial effects. Preferably, the compositions of the present disclosure are administered at a dosage and for a time such that the number and/or severity of the symptoms are decreased.

The pharmaceutical composition of the present disclosure may be administered to a subject in a dose from about 0.1 mg to about 1,000 mg per kilogram of body weight per day, such as 0.1, 0.5, 1, 2, 5, 7, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1,000 mg/Kg/day; preferably from about 0.5 to 500 mg per kilogram of body weight per day, such as 0.5, 2, 5, 7, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 50 mg/Kg/day; more preferably from about 1 to 100 mg per kilogram of body weight per day, such as 1, 2, 5, 7, 9, 10, 20, 30, 40, 50, 60, 70, 80, 90, and 100, mg/Kg/day. The dose may be administered once a day or be at least two, three, four, or five times a day.

Also within the scope of the present disclosure is a kit for improving kidney and/or heart function of a subject suffering from a kidney disease, such as AKI or CKD. The kit comprises in its container, (a) an effective amount of telbivudine, a salt, a solvate and/or an ester thereof; (b) one or more pharmaceutical acceptable carriers and/or excipients; and (c) instructions for using the kit to improve kidney and/or heart function of its recipients. The instructions may be in a form of pamphlet, tape, CD, VCD or DVD. According to certain embodiments, the telbivudine, a salt, a solvate and/or an ester thereof is in the form suitable for oral ingestion, subcutaneous infusion, intravenous administration, or inhalation.

The present invention will now be described more specifically with reference to the following embodiments, which are provided for the purpose of demonstration rather than limitation.

EXAMPLES

Materials and Methods

Animals

Sprague Dawley rats (7 weeks old) were kept in pathogen-free environment under 12:12 light-dark cycle with food and water provided ad libitum, ambient temperature and relative humidity were respectively set at 24±2° C. and 50±20%. All procedures involving animal studies of the present disclosure comply with the "Guideline for the Care and Use of Laboratory Animals" issued by The Chinese-Taipei Society of Laboratory Animal Sciences.

5/6 Nephrectomy

SD rats (about 10 weeks old) scheduled to undergo 5/6 nephrectomy or sham surgery were anesthetized by Zoletil 50/Xylazine (6 mg/1.3 mg/Kg, i.p.). Then, the left kidney was exposed, and the upper and lower poles were tied with a suture line, followed by right nephrectomy. The peritoneum and skin were then sutured, and the animals were returned to their individual cages. For animals underwent sham surgery, the left kidney was exposed in similar manner, but was then placed back into the abdominal cavity without further treatment, peritoneum and skin were then sutured. Two weeks after sham or 5/6 nephrectomy surgery, the animals were subjected to a 24-hour urine collection and non-invasive tail blood pressure measurement every 4 weeks. Four weeks after the surgery, rats underwent 5/6 nephrectomy or shame surgery were randomly assigned into two groups, i.e., the control and the telbivudine groups, in which the control group received saline treatment, and rats in the telbivudine group received telbivudine (10 mg/mL/Kg) treatment for 8 or 12 weeks. Animals were then sacrificed, and kidney and heart biopsy samples were obtained.

Cardiac Muscle Strain Measurement

Animals were placed into anesthesia chamber and anesthetized with isoflurane. Once the animal became unconscious, it was then connected to heart ultrasound machine (Vivid i, General Electric Company, US) and heart function paraments including changes in diastolic parameter—Tissue Velocity Imaging (TVI_V) and E/A ratio, the strain in cardia muscle (C_strain), and left ventrical mass (LVMASS) were respectively measured.

Western Blot Analysis

For protein identification, 30 μg nuclear extracted protein was loaded in each lane of the SDS-PAGE gel (8%) and separated by electrophoresis. The separated proteins were then electro-transferred to polyvinylidene fluoride (PVDF) membranes (GE Healthcare Bio-Sciences, Little Chalfont, UK), and blocked with 5% fat-free skim milk in TRIS-buffered saline containing 0.01% Tween-20 for 60 min at room temperature. The membrane was then incubated with rabbit polyclonalanti-IL-6, TGF-β, TIMP-1 and COL1-1 (diluted 1:1000 in PBS/5% skim milk; Novus. Biologicals) antibodies overnight at 4, respectively. HRP conjugated anti-rabbit IgG (Promega) was then used as secondary antibody. Immunoreactive protein was visualized by the chemiluminescence protocol (ECL, GE HealthcareBio-Sciences). Anti-actin rabbit polyclonal antibody (1:1000; Sigma-Aldrich) was used for calibration.

Quantitative RT-PCR

Total RNA was extracted from fresh frozen renal and heart tissues using the Trizol Reagent (Life Technologies), according to the manufacturer protocol. Briefly, renal cortex or heart tissue (150 mg) was homogenized with 1 ml Trizol, and RNA-containing aqueous phase was obtained by centrifugation. Following the precipitation of RNA by centrifugation with 0.5 volume isopropanol and purification with 75% ethanol, the extracted total RNA was dissolved in 80 μL nuclease-free deionized distilled water and stored at −20° C. The concentration and purity of RNA were determined by Nanodrop Spectrophotometer (Thermo Scientific). First-strand cDNAs were synthesized from template RNA (1 μg) using Transcriptor First Strand cDNA Synthesis Kit (Roche), according to the manufacturer's protocol. Real-time PCR was performed using 2 μL template in a 20-μL reaction containing 1 μM of each primer and 10 μLLightCyclerFastStartUniversal SYBR Green Master (ROX) (Roche).

The following LightCycler® 96 conditions were used: Pre-incubation at 95° C. for 10 min, followed by 40 cycles with 2 Step Amplification at 95° C. for 10 s, 60° C. for 30 s, and Melting at 95° C. for 10 s, 65° C. for 60 s, 97° C. for 1 s, and Cooling at 37° C. for 30 s (Roche). GAPDH was used as a housekeeping gene for normalizing the expression data.

Example 1 Telbivudine Improves Kidney and/or Heart Function in CKD Rats

In this example, to evaluate the therapeutic function of telbivudine, animals were first subject to 5/6 nephrectomy to induce in vivo kidney failure before being treated with telbivudine.

5/6 nephrectomy is a procedure in which one kidney of a test animal is removed and 2/3 of the remaining kidney is ablated, thereby mimics the progressive renal failure after loss of renal mass in humans. Briefly, approximately 50% of the remaining kidney of the rat was removed by polar excision 1-2 weeks after uni-nephrectomy. Then, the animals were randomly assigned to two groups, the telbivudine group and the control group. Rats in the telbivudine group were orally fed with telbivudine (at a dosage of 100 mg/Kg) for 4, 8 or 12 weeks, while the animals in the control group were given just the water. Blood and urine samples were respectively collected on designated days and analyzed for the levels of blood urine nitrogen (BUN), serum creatine (CR), and hepatic enzymes (i.e., alanine aminotransferase (ALT) and aspartate aminotransferase (AST)). Heart function was determined by monitoring the changes in diastolic parameter—Tissue Velocity Imaging (TVI_V), E/A ratio, and the strain in cardia muscle (C_strain), left ventrical mass (LVMASS). Animals were sacrificed after the experiments were finished, and kidney biopsy samples were obtained.

1.1 Telbivudine Improves Kidney Function in CKD Rats

Figure 1:
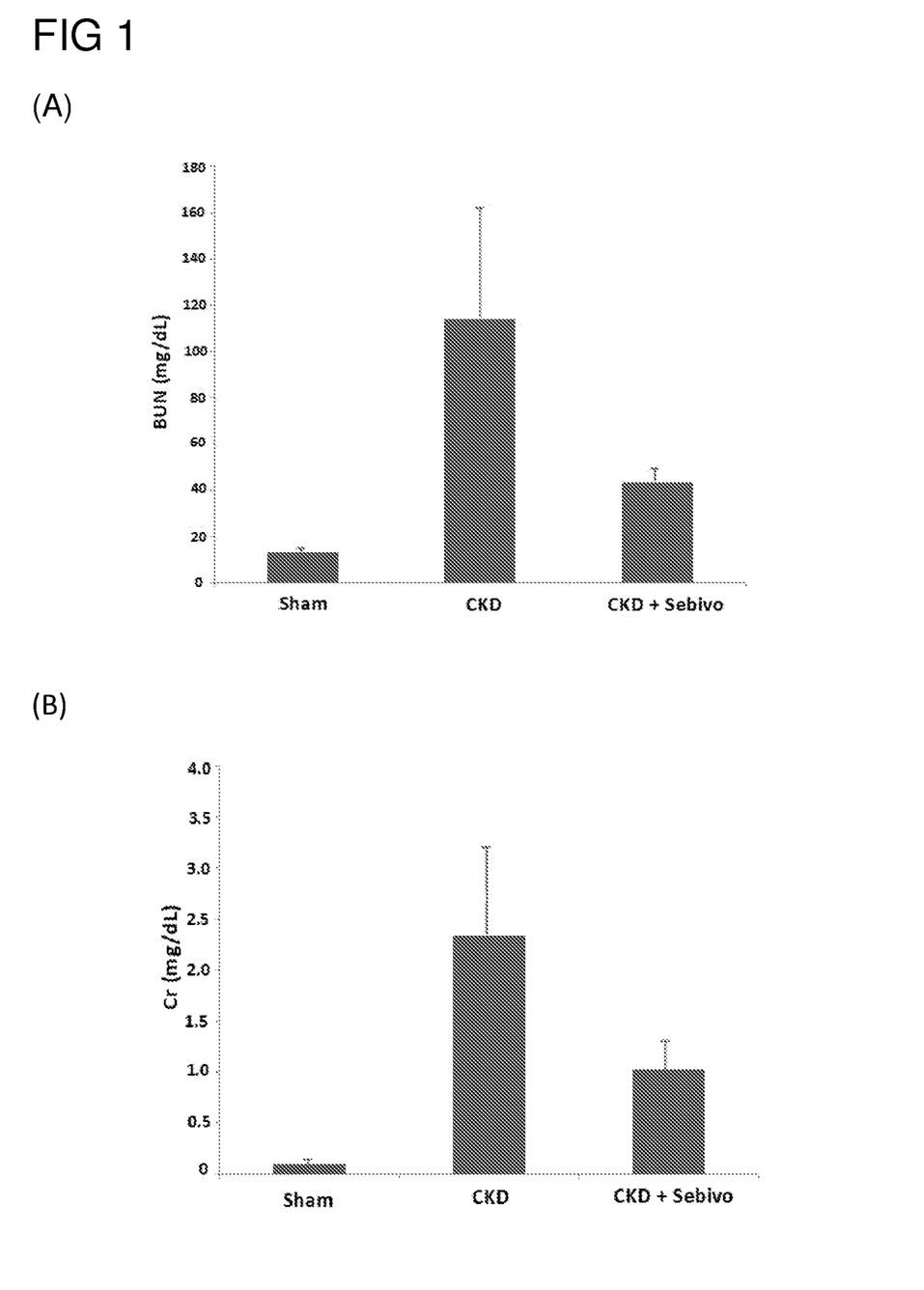
FIG. 1 illustrates the effect of telbivudine on the levels of (A) urine nitrogen and (B) serum creatine in CKD rats in accordance with one embodiment of the present disclosure.

Referring to results depicted in FIG. 1, the levels of BUN and CR in animals underwent 5/6 nephrectomy were respectively about 4 and 10 folds of those of the control animals at week 8, and continued to rise until week 12. By contrast, animals treated with telbivudine for 8 weeks exhibited significant reduction in both the levels of BUN and CR, and the effect was most significant when telbivudine was given for 12 weeks.

Figure 2:
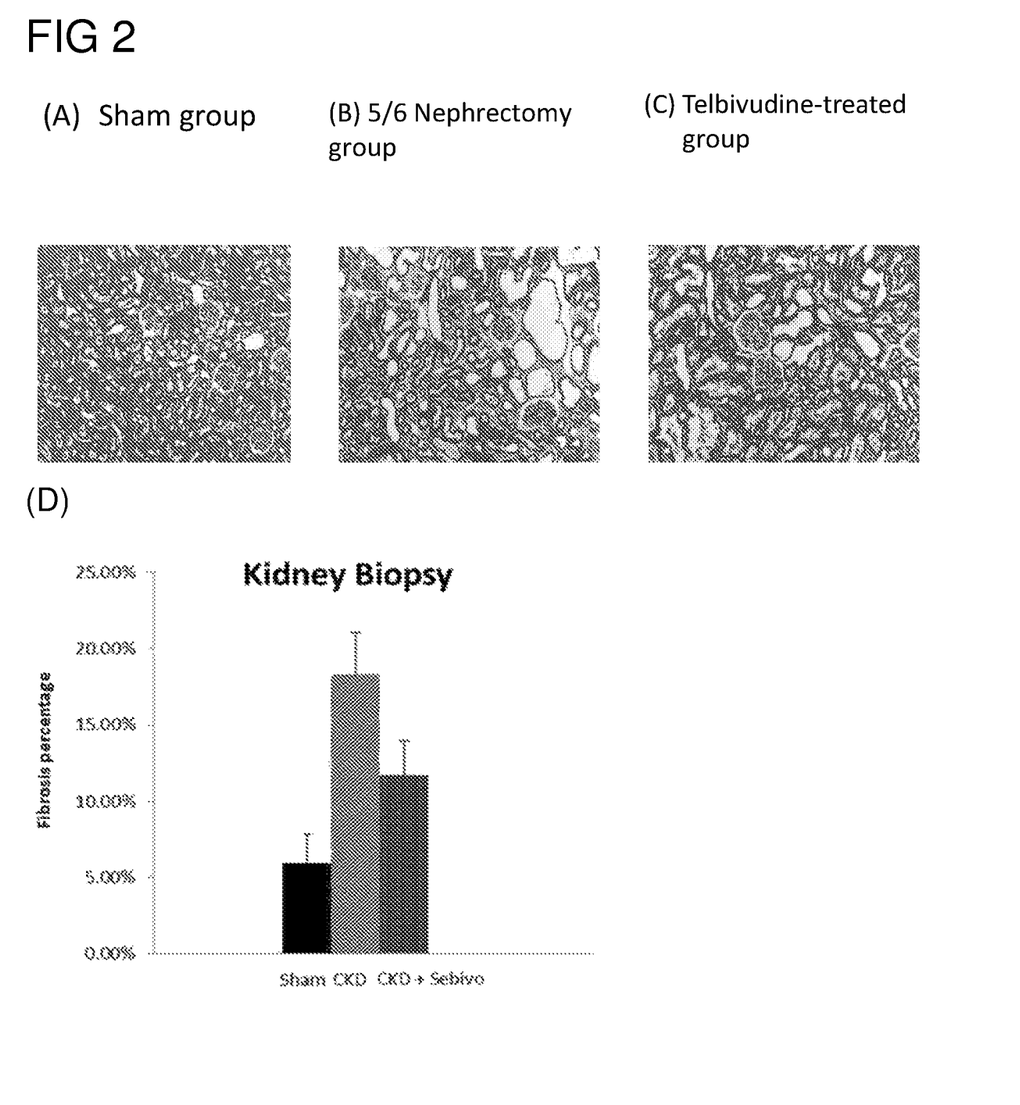
FIG. 2 illustrates the effects of the telbivudine on kidney function of CKD rats, in which (A) to (C) are photographs of kidney samples respectively taken from the healthy rats, un-treated CKD rats, and telbivudine-treated CKD rats; and (D) is a bar graph illustrating the quantitated results of kidney fibrosis in the control rats, CKD rats or telbivudine-treated CKD rats after 8 or 12 weeks in accordance with one embodiment of the present disclosure, in which $p<0.05$ for CKD vs CKD+sebivo group.

The photographs in FIG. 2 are kidney samples respectively taken from the healthy rats, CKD rats, and telbivudine-treated CKD rats. 5/6 nephrectomy resulted in fibrosis in kidney tissues (FIG. 2, panel A vs panel B), and telbivudine treatment significantly reduced the extent of kidney fibrosis in CKD rats (FIG. 2, panel B vs panel C). The quantitative results of the telbivudine treatment indicated that the extents of kidney fibrosis decreased for about 62.4% and 79.2% in CKD animals receiving telbivudine treatment for 8 and 12 weeks, respectively (FIG. 2, panel D).

Figure 3:
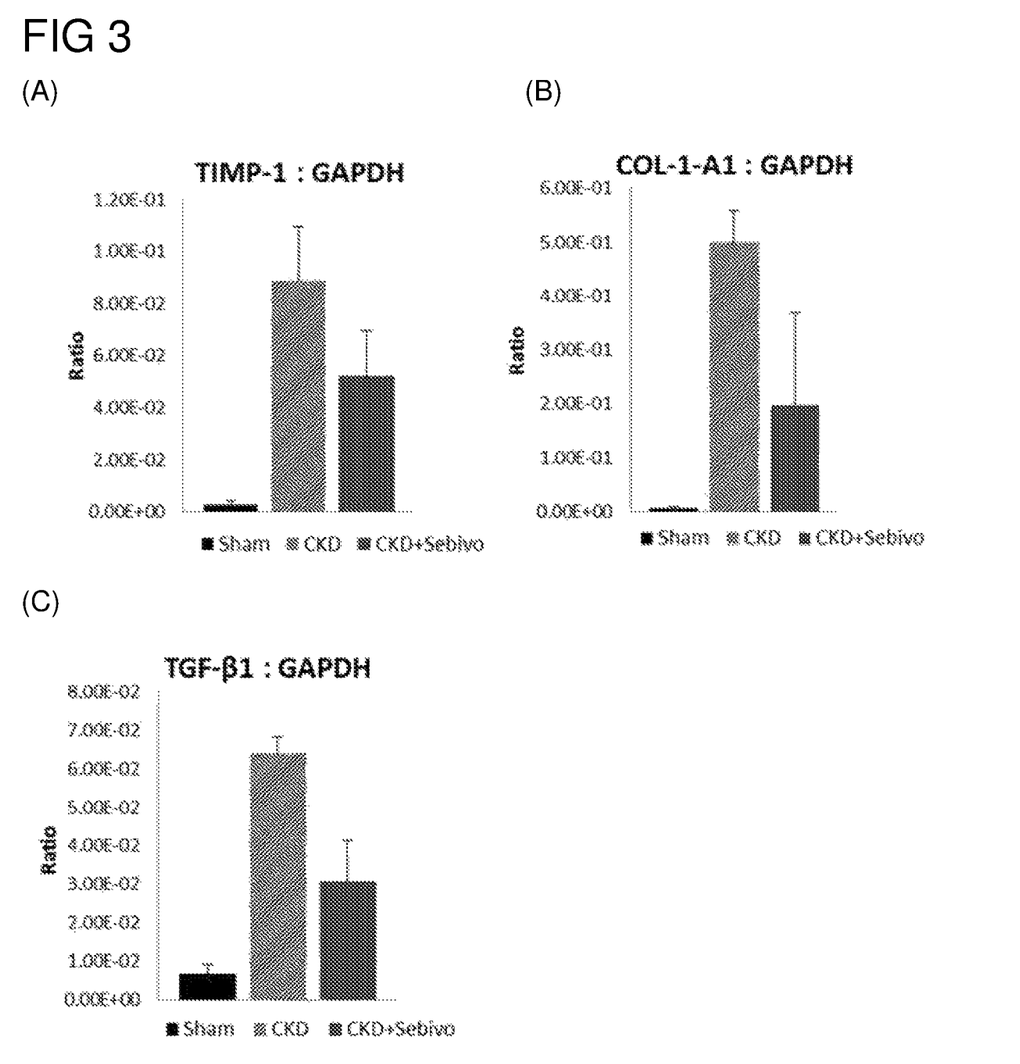
FIG. 3 illustrates the effects of the telbivudine on the mRNA levels of (A) TIMP-1, (B) COL-1-A1 and (C) TGF-β1 in kidney tissue of CKD rats in accordance with one embodiment of the present disclosure.
Figure 4:
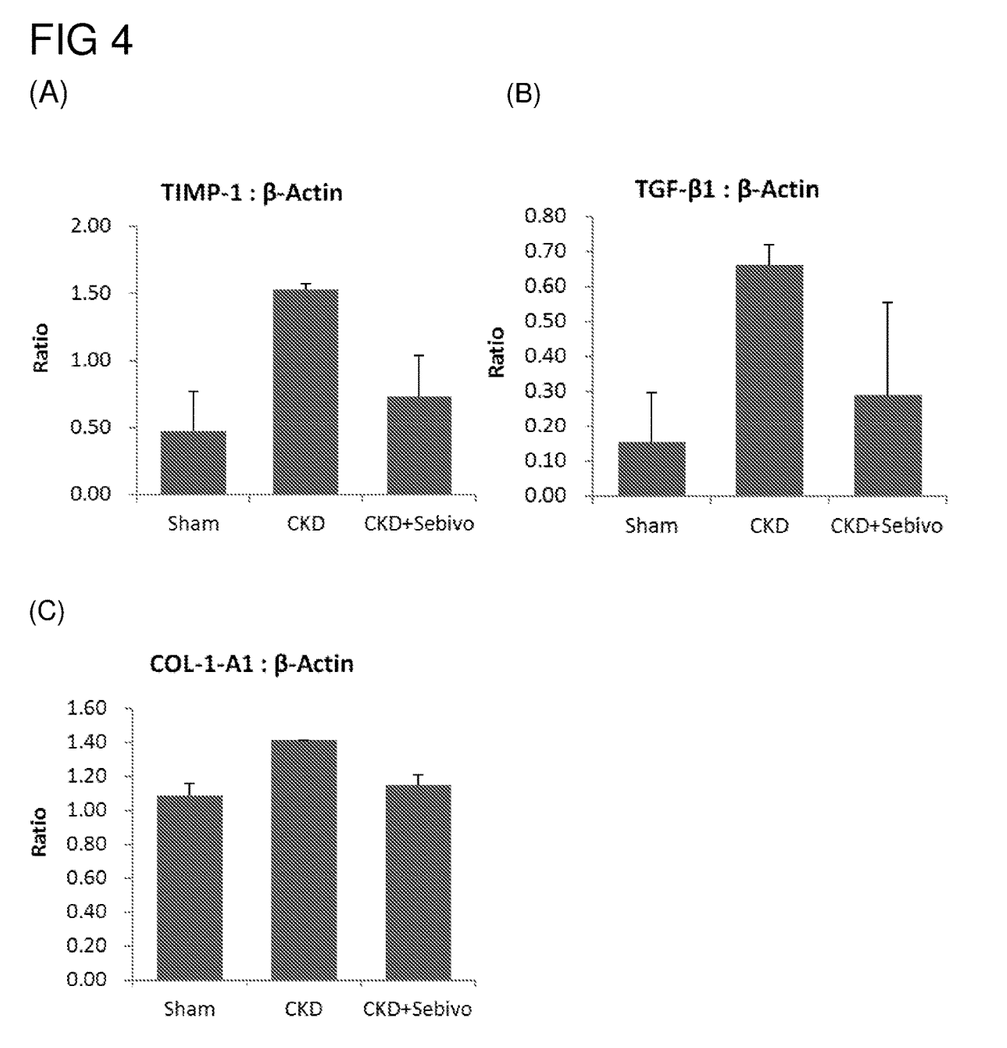
FIG. 4 illustrates the effects of the telbivudine on the protein levels of (A) TIMP-1, (B) COL-1-A1 and (C) TGF-β1 in kidney tissue of CKD rats in accordance with one embodiment of the present disclosure.

In addition, the data in the present study demonstrated that telbivudine improved kidney function by reducing the expression of inflammatory genes and/or proteins, in which both the mRNA and the protein levels of IL-6, TGF-β, TIMP1 and COL-1-A1 were reduced (FIGS. 3 and 4).

Taken together, the data confirmed that telbivudine may improve the kidney function in CKD rats by suppressing the expression levels of inflammatory genes, which include but are not limited to, the genes of IL-6, TGF-β, TIMP1 and COL-1-A1.

1.2 Telbivudine Improves Heart Function in CKD Rats

Figure 5:
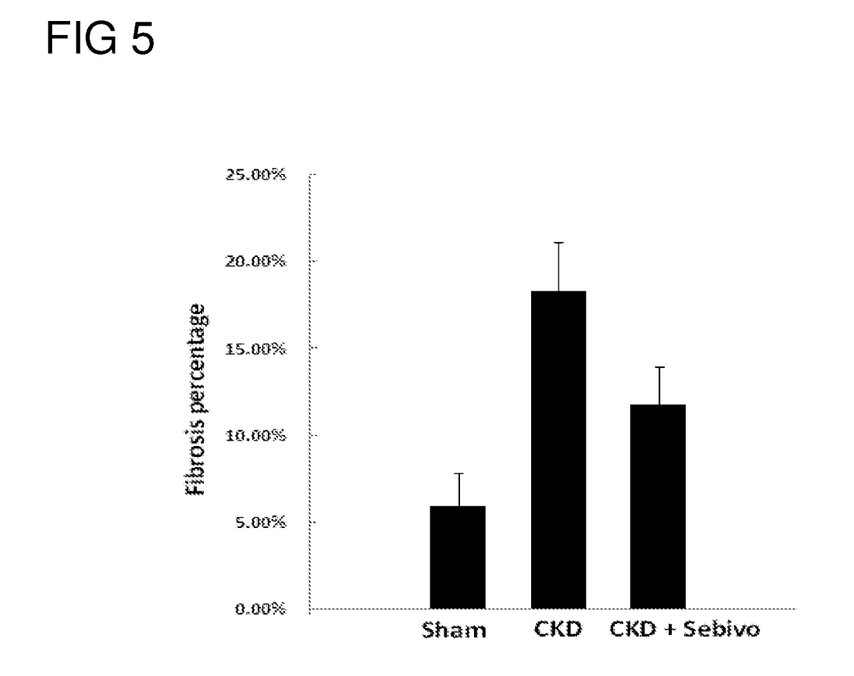
FIG. 5 illustrates the effects of the telbivudine on heart fibrosis in CKD rats in accordance with one embodiment of the present disclosure.

Similar to the finding in example 1.1, 5/6 nephrectomy resulted in fibrosis in the heart tissue of CKD rats, and the extent of fibrotic tissues was markedly reduced in telbivudine-treated CKD rats (FIG. 5).

Figure 6A:
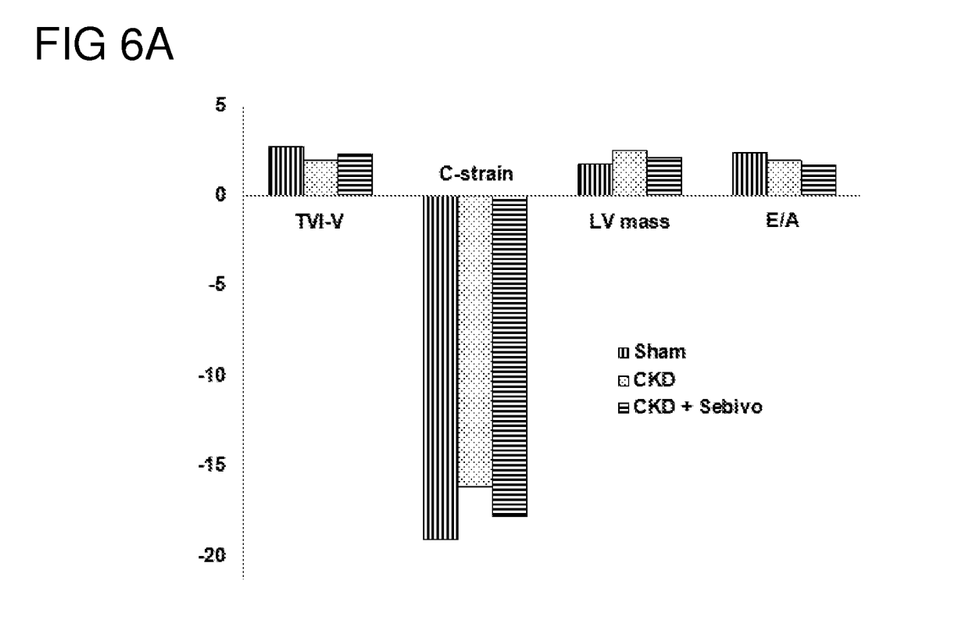
FIG. 6A illustrates the effects of the telbivudine on diastolic parameters including Tissue Velocity Imaging (TVI_V), the strain in cardia muscle (C_strain), left ventrical mass (LVMASS), and E/A ratio in CKD rats in accordance with one embodiment of the present disclosure, in which $p<0.05$ for CKD vs CKD+sebivo group.
Figure 6B:
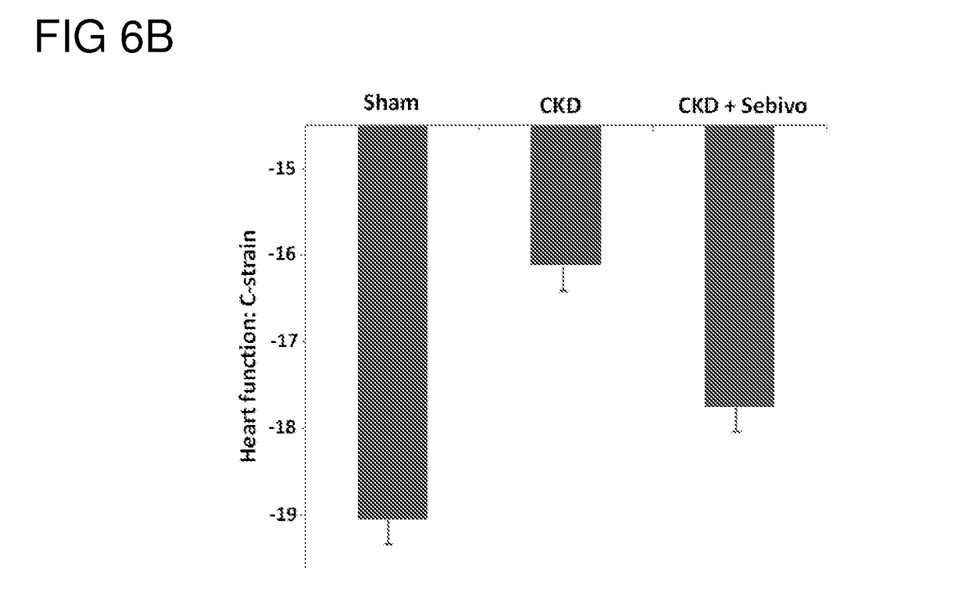
FIG. 6B illustrates the changes in the cardia muscle strain (C_strain) in CKD rats treated with telbivudine for 8 or 12 weeks in accordance with one embodiment of the present disclosure, in which $p<0.05$ for CKD vs CKD+sebivo group.

FIG. 6A depicts the changes of four cardiac parameters including diastolic parameters including Tissue Velocity Imaging (TVI_V), the strain in cardia muscle (C_strain), left ventrical mass (LVMASS), and E/A ratio, measured by heart ultrasound before and after 12-week treatment with telbivudine in rats underwent 5/6 nephrectomy or sham surgery. FIG. 6B depicts the effect of telbivudine treatment on the C-strain values in animals underwent sham surgery or 5/6 nephrectomy. As evidence in this example, CKD animals treated with telbivudine for 8 or 12 weeks exhibited significant improvement in C-strain values, as compared with that of the control animals.

Figure 7:
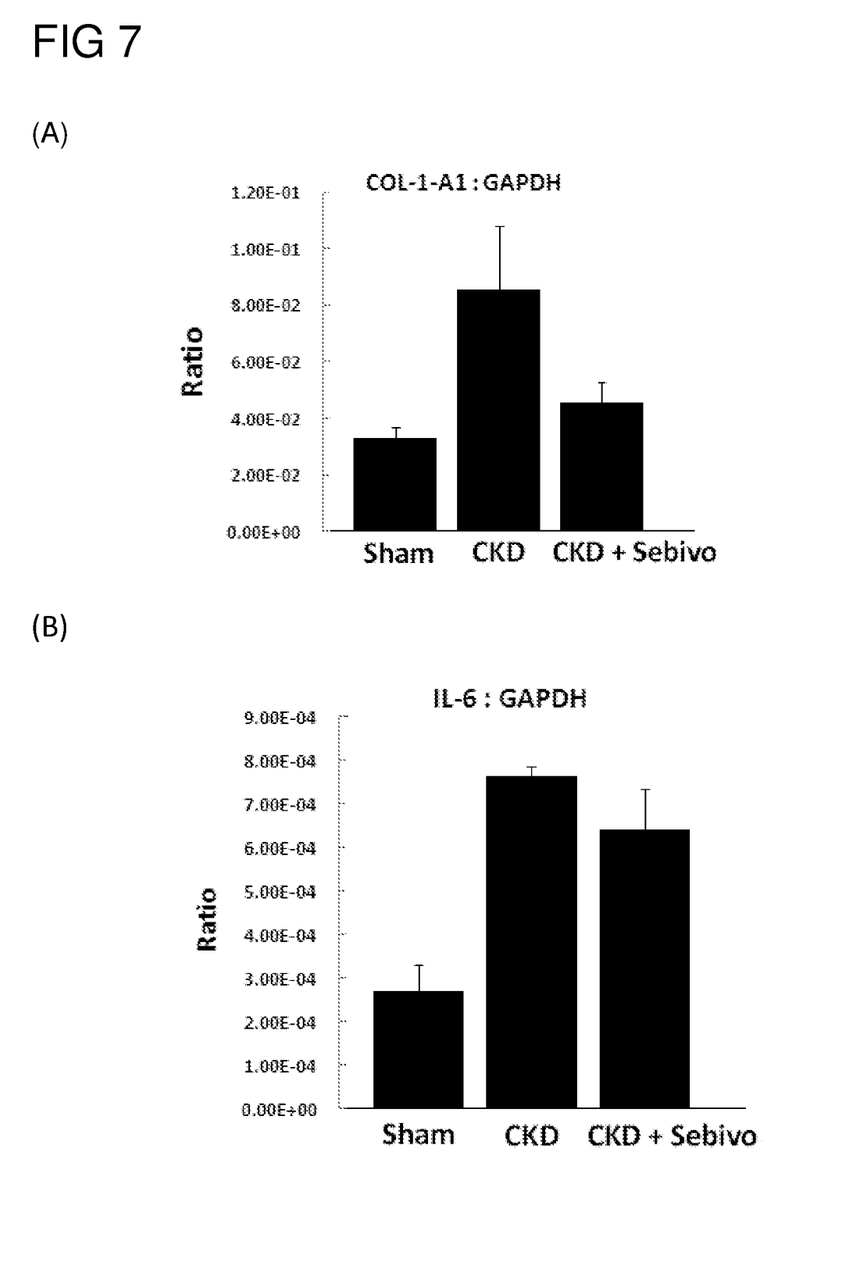
FIG. 7 illustrates the effects of the telbivudine on the mRNA levels of (A) COL-1-A1 and (B) IL-6 in heart tissue of CKD rats in accordance with one embodiment of the present disclosure.
Figure 8:
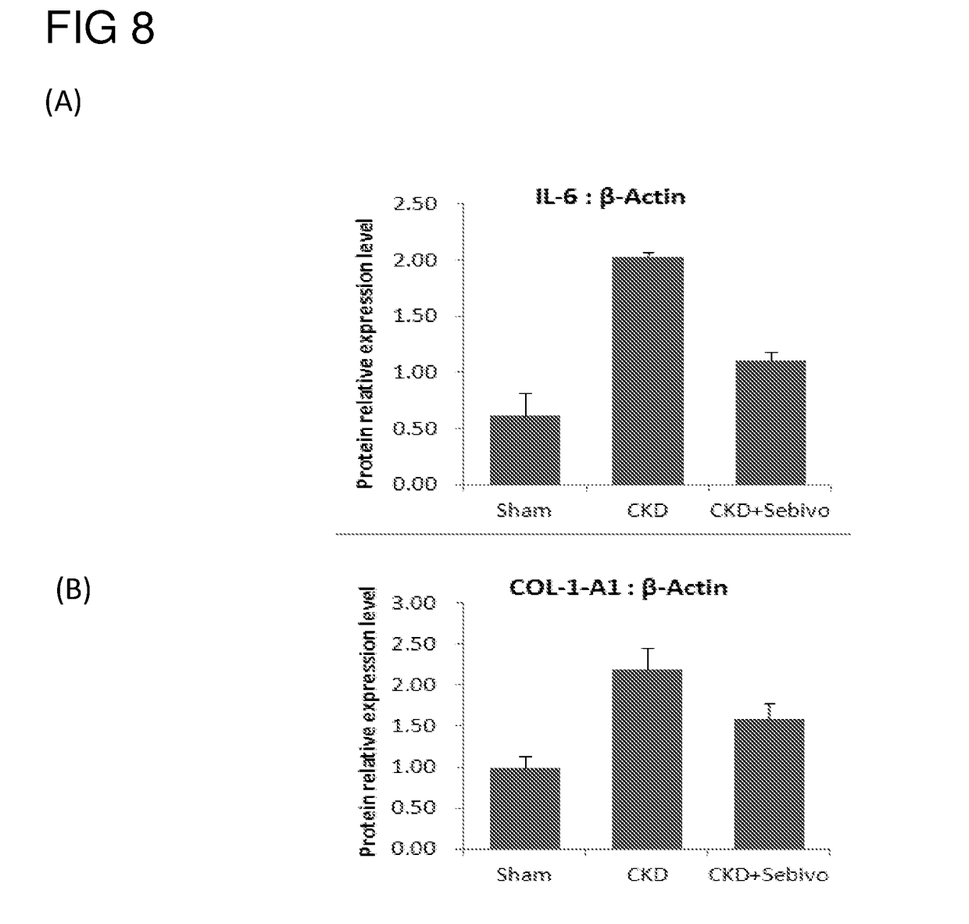
FIG. 8 illustrates the effects of the telbivudine on the protein levels of (A) IL-6 and (B) COL-1-A1 in heart tissue of CKD rats in accordance with one embodiment of the present disclosure.

In addition, similar to finding in example 1.1, telbivudine improved heart function also by reducing the expression of inflammatory genes and/or proteins, in which both the mRNA and the protein levels of IL-6, and COL-1-A1 were markedly reduced in telbivudine-treated tissues (FIGS. 7 and 8).

Taken together, the results in this example demonstrated that telbivudine may improve heart function of CKD animals.

Example 2 Telbivudine Reduces the Level of Uremic Toxins in CKD Rats

Indoxyl sulfate (IS) and P-cresyl sulfate (PCS) are uremic toxins that accumulate in the serum of CKD patients, and are known factors for causing heart problems in the CKD subjects.

Figure 9A:
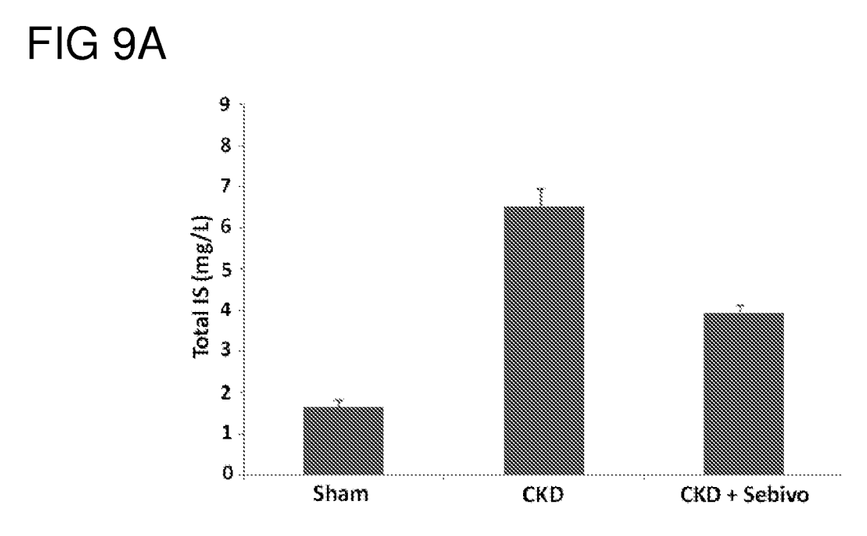
FIG. 9A illustrate the respective effects of telbivudine on the toal level of Indoxyl sulfate (IS) in the serum collected from CKD rats in accordance with one embodiment of the present disclosure, in which $p<0.05$ for CKD vs CKD+sebivo group.
Figure 9B:
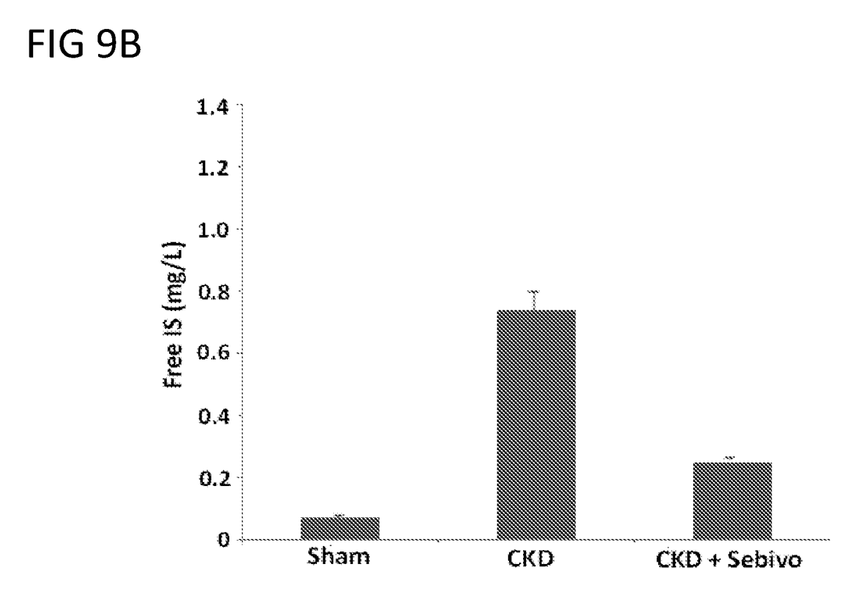
FIG. 9B illustrate the respective effects of telbivudine on the free level of Indoxyl sulfate (IS) in the serum collected from CKD rats in accordance with one embodiment of the present disclosure, in which $p<0.05$ for CKD vs CKD+sebivo group.
Figure 9C:
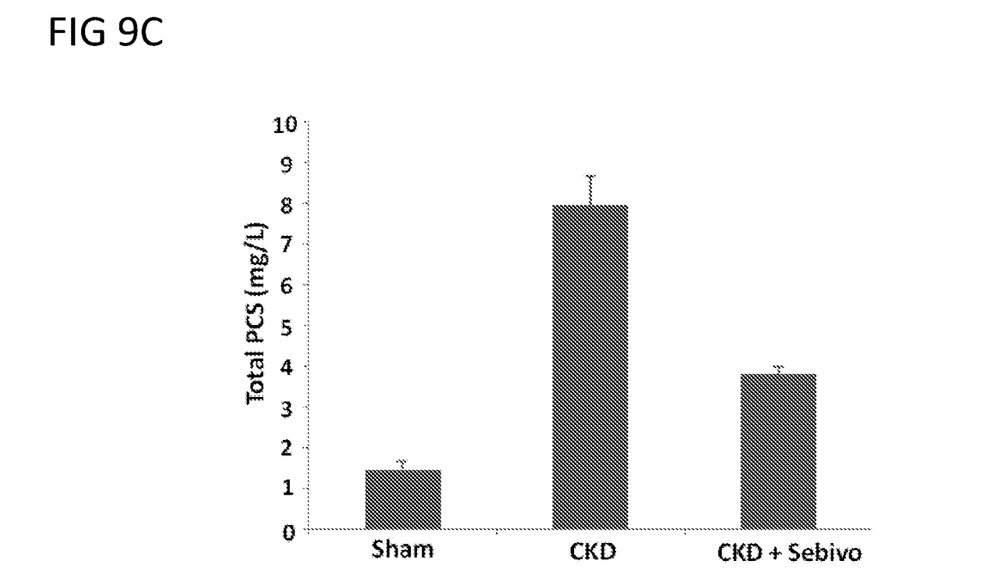
FIG. 9C illustrate the respective effects of telbivudine on the total level of P-cresyl sulfate (PCS) in the serum collected from CKD rats in accordance with one embodiment of the present disclosure, in which $p<0.05$ for CKD vs CKD+sebivo group.
Figure 9D:
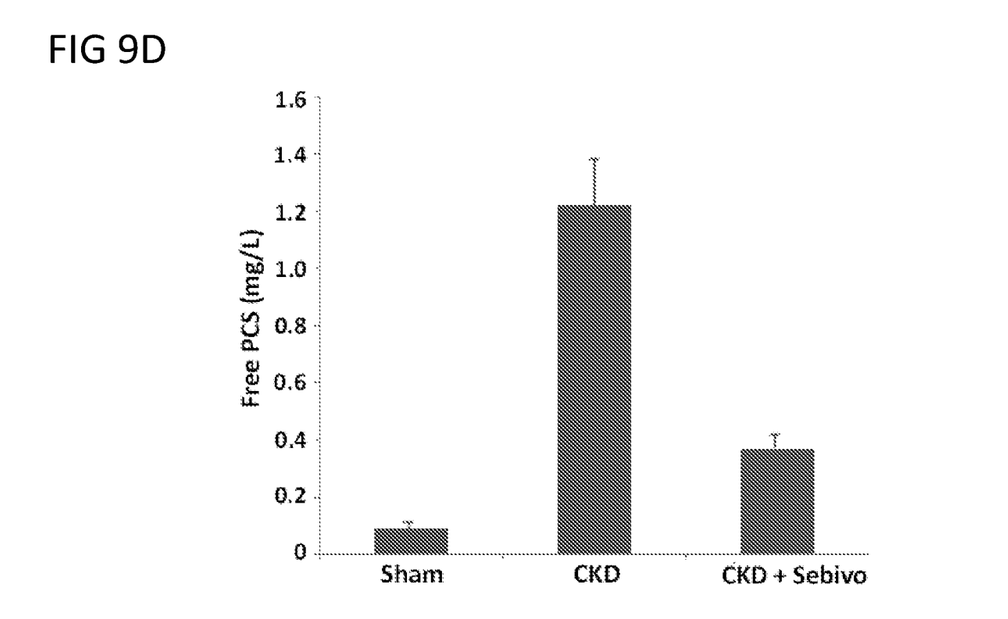
FIG. 9D illustrate the respective effects of telbivudine on the free level of P-cresyl sulfate (PCS) in the serum collected from CKD rats in accordance with one embodiment of the present disclosure, in which $p<0.05$ for CKD vs CKD+sebivo group.

FIGS. 9A and 9C illustrate the effects of telbivudine on the toal levels of Indoxyl sulfate (IS) and P-cresyl sulfate (PCS) in the serum collected from CKD rats; whereas the effects of telbivudine on the free level of IS and PCS are depicted in FIGS. 9B and 9D.

As evidenced from the data, telbivudine effectively reduced both the total and free levels of uremic toxins (i.e., PCS and IS). Thus, the data presented in this example indicates that telbivudine may improve heart function of a CKD subject by reducing the level of accumulated uremic toxins in such patient.

Example 3 Telbivudine Possesses No Toxic Effects Toward Liver Function

In this example, the effect of telbivudine on liver function was investigated.

Figure 10:
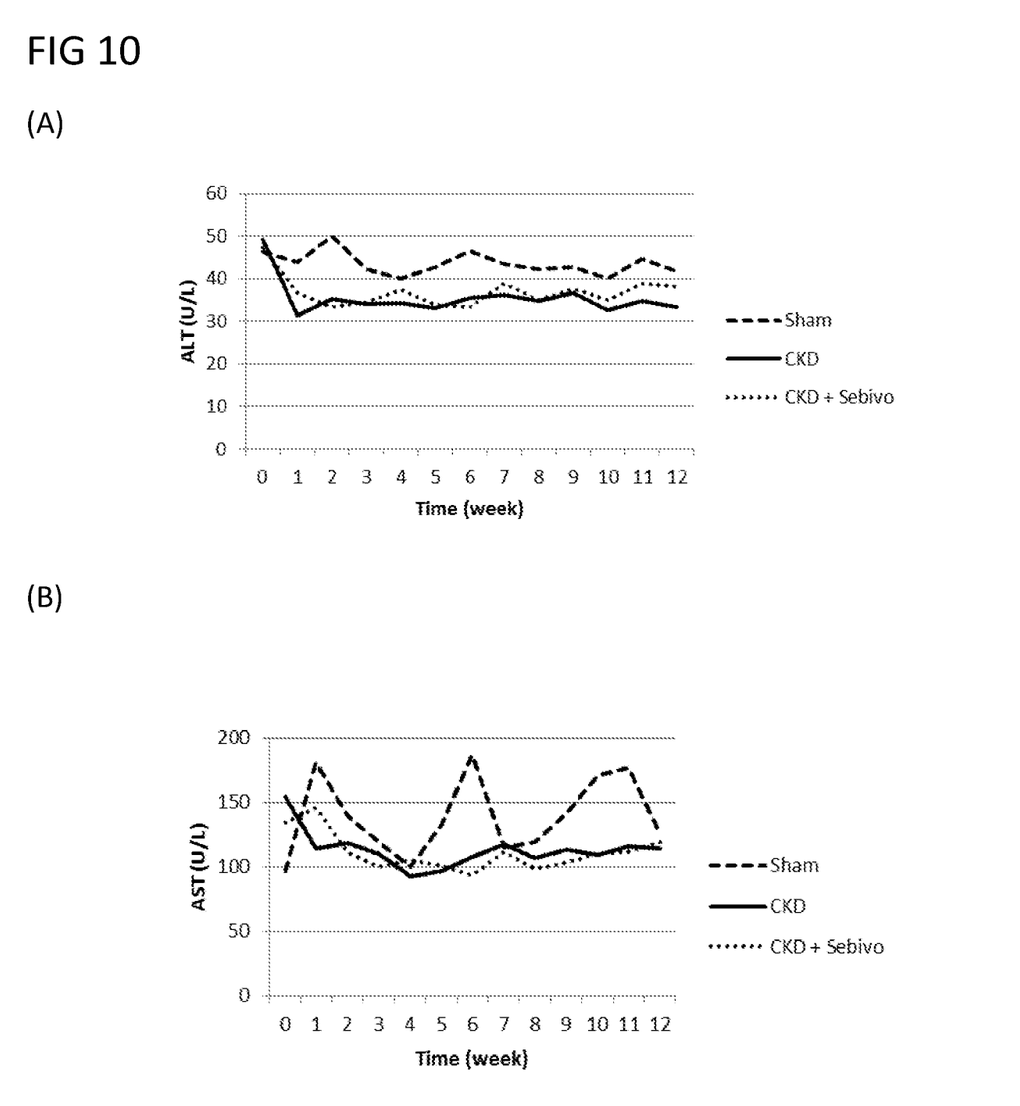
FIG. 10 illustrate the effect of telbivudine on the levels of (A) alanine aminotransferase (ALT) and (B) aspartate aminotransferase (AST) in the serum collected from CKD rats in accordance with one embodiment of the present disclosure.

Data in FIG. 10 demonstrates that telbivudine does not possess any toxic effects toward liver function, as the levels of lipatic enzymes, i.e., alanine aminotransferase (ALT) and aspartate aminotransferase (AST), remained relatively the same as compared with those of the control animals. (FIG. 10, panels A and B)

In sum, the data in the present study confirms that telbivudine may be used to treat CKD subject and/or prevent CKD subject from developing heart problems associated with and/or secondary to CKD.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of improving the heart fibrosis of a subject suffering from AKI or CKD comprising administering to the subject an effective amount of telbivudine, a salt, a solvate, and/or an ester thereof, wherein the administration of the effective amount of the telbivudine, the salt, the solvate, and/or the ester thereof improves the heart fibrosis of the subject.

2. The method of claim 1, wherein the telbivudine, the salt, the solvate, and/or the ester thereof is administered to the subject in a dose of about 0.1 to 1,000 mg/Kg/day.

3. The method of claim 2, wherein the telbivudine, the salt, the solvate, and/or the ester thereof is administered to the subject in a dose of about 0.5 to 500 mg/Kg/day.

4. The method of claim 1, wherein the telbivudine, the salt, the solvate, and/or the ester thereof is administered to the subject via oral, enteral, or parenteral administration.

5. The method of claim 4, wherein the parenteral administration is any of intramuscular, intravenous, or intraperitoneal injection.

6. The method of claim 1, wherein the subject is a human.

* * * * *